United States Patent
Chevalier et al.

(10) Patent No.: US 10,813,865 B2
(45) Date of Patent: Oct. 27, 2020

(54) LIQUID MIXTURE CONTAINING 4-(3-ETHOXY-4-HYDROXYPHENYL) BUTAN-2-ONE AND XANTHINE COMPOUND

(71) Applicant: L'OREAL, Paris (FR)

(72) Inventors: Veronique Chevalier, Chevilly la Rue (FR); Sofiane Ouattara, Chevilly la Rue (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/311,957

(22) PCT Filed: Jun. 23, 2017

(86) PCT No.: PCT/EP2017/065550
§ 371 (c)(1),
(2) Date: Dec. 20, 2018

(87) PCT Pub. No.: WO2018/001899
PCT Pub. Date: Jan. 4, 2018

(65) Prior Publication Data
US 2019/0201313 A1    Jul. 4, 2019

(30) Foreign Application Priority Data

Jun. 30, 2016 (FR) ..................... 16 56176

(51) Int. Cl.
| A61K 8/49 | (2006.01) |
| A61K 8/35 | (2006.01) |
| A61Q 19/10 | (2006.01) |
| A61Q 9/02 | (2006.01) |
| A61Q 5/12 | (2006.01) |
| A61Q 19/00 | (2006.01) |
| A61Q 5/02 | (2006.01) |
| A61Q 1/00 | (2006.01) |
| A61Q 5/06 | (2006.01) |
| A61Q 9/00 | (2006.01) |

(52) U.S. Cl.
CPC .............. *A61K 8/4953* (2013.01); *A61K 8/35* (2013.01); *A61Q 1/00* (2013.01); *A61Q 5/02* (2013.01); *A61Q 5/06* (2013.01); *A61Q 5/12* (2013.01); *A61Q 9/00* (2013.01); *A61Q 9/02* (2013.01); *A61Q 19/00* (2013.01); *A61Q 19/002* (2013.01); *A61Q 19/10* (2013.01); *A61K 2800/49* (2013.01); *A61K 2800/524* (2013.01)

(58) Field of Classification Search
CPC .... A61K 8/4953; A61K 8/35; A61K 2800/49; A61K 2800/524; A61Q 5/02; A61Q 19/00; A61Q 5/12; A61Q 9/02; A61Q 19/002; A61Q 9/00; A61Q 5/06; A61Q 1/00; A61Q 19/10
See application file for complete search history.

(56) References Cited

FOREIGN PATENT DOCUMENTS

| DE | 25 59 384 A1 | 7/1977 |
| FR | 2973227 | * 10/2012 |
| WO | WO-2012/130953 A1 | 10/2012 |
| WO | WO-2012/130954 A1 | 10/2012 |

* cited by examiner

*Primary Examiner* — Sahar Javanmard
(74) *Attorney, Agent, or Firm* — Polsinelli PC

(57) ABSTRACT

The invention relates to a liquid mixture containing 4-(3-ethoxy-4-hydroxyphenyl)butan-2-one and a xanthine compound, and also to a cosmetic composition containing such a mixture. Use for caring for, making up and cleansing keratin materials.

23 Claims, No Drawings

LIQUID MIXTURE CONTAINING 4-(3-ETHOXY-4-HYDROXYPHENYL) BUTAN-2-ONE AND XANTHINE COMPOUND

CROSS REFERENCE TO RELATED APPLICATIONS

This application is the National Phase of Application No. PCT/EP2017/065550 filed Jun. 23, 2017, which claims priority to Application No. 16 56176 filed in France on Jun. 30, 2016 under 35 U.S.C. § 119. The entire contents of each application are hereby incorporated by reference.

The subject of the present invention is a liquid mixture containing 4-(3-ethoxy-4-hydroxy-phenyl)butan-2-one and a xanthine compound, and also a cosmetic composition containing such a mixture.

4-(3-Ethoxy-4-hydroxyphenyl)butan-2-one (ketone compound) is an interesting substance as a preserving agent for cosmetic compositions, for protecting the compositions against microbial contamination, as described in the application WO 2011/039445.

Nonetheless at room temperature (23° C.) this compound is in the form of a very compact amorphous solid which is not readily taken up, making its handling difficult, especially for industrial manufacturing of products, such as compositions (mixtures of ingredients) comprising this compound. Moreover, this compound is very sparingly soluble in water or in glycerol, or else even in 2-octyldodecanol, and it is known from documents WO2012/130953 and WO2012/130954 to use certain organic solvents in order to be able to dissolve this ketone compound and facilitate the use thereof in compositions of mixtures of ingredients. In order to dissolve the ketone compound, it is for example necessary to use 1,3-propanediol, one of the best solvents, in a large amount relative to the amount of ketone compound, namely at least 40% by weight of 1,3-propanediol per 60% by weight of ketone compound, i.e. a weight ratio of ketone compound/1,3-propanediol=1.5. Thus, dissolution by an organic solvent requires the use of large amounts of solvent relative to the amount of ketone compound to be dissolved. This large amount of solvent has a restrictive effect on the industrial manufacture of products containing the ketone compound dissolved with the solvents: restrictions in terms of space (the ketone compound and solvent mixture is voluminous and requires manufacturing tanks of large volume) and in terms of cost associated with this large amount of solvent to be used.

It therefore appears to be necessary to be able to use the ketone compound more easily than by the route of dissolution with an organic solvent. It is especially sought to be able to provide a simple liquid mixture comprising the ketone compound, which is readily usable and also having good stability, in order to avoid any phenomenon of recrystallization of the ketone compound during storage of said liquid mixture.

The inventors have discovered, unexpectedly, that the combination of 4-(3-ethoxy-4-hydroxyphenyl)butan-2-one with a xanthine compound such as caffeine in specific proportions makes it possible to obtain a mixture in liquid form, in which the ketone compound does not crystallize, especially after storage for at least 2 months at room temperature (23° C.). This liquid mixture is easy to use in compositions and thus enables easier industrial manufacture of the compositions containing the ketone compound.

More specifically, a subject of the invention is a liquid mixture comprising, or constituted of (or consisting of), 4-(3-ethoxy-4-hydroxyphenyl)butan-2-one and a xanthine compound (I) as defined below, especially present at an amount such that the weight ratio of 4-(3-ethoxy-4-hydroxyphenyl)butan-2-one/compound (I) ranges from 17 to 250.

Another subject of the invention is a composition, especially a cosmetic composition, comprising, in a physiologically acceptable medium, said mixture described above.

A further subject of the invention is a process for the non-therapeutic cosmetic treatment of keratin materials, comprising the application to the keratin materials of a composition as described above. The process may be a cosmetic process for caring for or making up or cleansing keratin materials.

4-(3-Ethoxy-4-hydroxyphenyl)butan-2-one is a compound of formula:

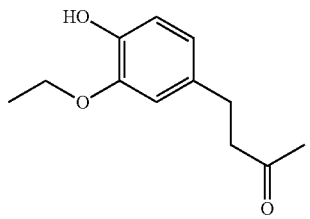

The xanthine compound is a compound of formula (I) below:

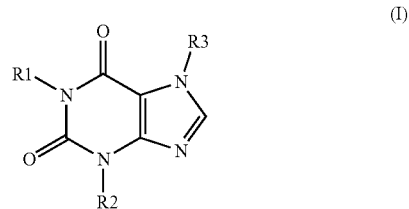

wherein:

R1, R2 and R3, independently of one another, denote a hydrogen atom or a methyl or ethyl radical, preferably a hydrogen atom or a methyl radical, and more preferentially a methyl radical.

The compound (I) may be xanthine (R1=R2=R3=H), caffeine (R1=R2=R3=methyl), theobromine (R1=H; R2=R3=methyl), theophylline (R1=R2=methyl; R3=H) and paraxanthine (R1=R3=methyl; R2=H).

Advantageously, the xanthine compound (I) is caffeine.

In the mixture according to the invention, the weight ratio of 4-(3-ethoxy-4-hydroxy-phenyl)butan-2-one/compound (I) preferably ranges from 17 to 200, and preferentially from 17 to 100.

The compound 4-(3-ethoxy-4-hydroxyphenyl)butan-2-one may be present in the composition according to the invention at an amount ranging from 0.01% to 5% by weight relative to the total weight of the composition, preferably ranging from 0.01% to 3% by weight, and preferentially ranging from 0.01% to 2.5% by weight.

The mixture is liquid and homogeneous, it is easy to handle and thereby enables easy incorporation of the ketone compound with other additional ingredients to prepare compositions such as cosmetic or dermatological compositions.

Another subject of the invention is a process for preparing a liquid mixture comprising a step of mixing 4-(3-ethoxy-4-hydroxyphenyl)butan-2-one and xanthine compound (I) heated to a temperature of between 70 and 80° C., then a step of cooling to a temperature of between 15 and 28° C., in particular between 20 and 25° C. (room temperature).

Another subject of the invention is a composition comprising, in a physiologically acceptable medium, the liquid mixture described above.

Physiologically acceptable medium is intended to mean a medium that is compatible with human keratin materials such as the skin, the scalp, the hair and the nails. Said medium may comprise one or more additional ingredients different from the ketone compound and from the xanthine compound (I).

The composition may comprise at least one additional ingredient chosen from water, oils, polyols having from 1 to 10 carbon atoms, gelling agents, surfactants, film-forming polymers, colorants, fragrances, fillers, UV screening agents, plant extracts, cosmetic and dermatological active agents, and salts.

The composition according to the invention may comprise an aqueous phase.

The composition may comprise water, which may be present at an amount ranging from 5% to 80% by weight relative to the total weight of the composition, and preferably ranging from 35% to 75% by weight.

The composition may also comprise a polyol that is water-miscible at room temperature (25° C.), especially chosen from polyols especially having from 2 to 10 carbon atoms, preferably having from 2 to 6 carbon atoms, such as glycerol, propylene glycol, 1,3-propanediol, butylene glycol, pentylene glycol, hexylene glycol, dipropylene glycol, diethylene glycol, or diglycerol.

The compositions according to the invention may be in the form of oil-in-water (O/W) emulsions, water-in-oil (W/O) emulsions or multiple emulsions (triple: W/O/W or O/W/O), oily solutions, oily gels, aqueous solutions, aqueous gels, solid compositions. These compositions are prepared according to the usual methods.

The compositions according to the invention may be more or less fluid and may have the appearance of a white or coloured cream, an ointment, a milk, a lotion, a serum, a paste or a foam. They may be optionally applied to the skin in aerosol form. They may also be in solid form, for example in the form of a stick or a compact powder.

The composition according to the invention may especially be in the form of:
- a makeup product, especially for making up the skin of the face, the body, or the lips or the eyelashes;
- an aftershave gel or lotion;
- a hair-removing cream;
- a body hygiene composition such as a shower gel or a shampoo;
- a pharmaceutical composition;
- a solid composition such as a soap or a cleansing bar;
- an aerosol composition also comprising a pressurized propellant;
- a hair-setting lotion, a hair-styling cream or gel, a dyeing composition, a hair-restructuring lotion, a permanent-wave composition, a lotion or a gel for combating hair loss; or
- a composition for caring for or cleansing the skin.

Another subject of the invention is a process for preparing a composition, especially a cosmetic or dermatological composition, comprising:
a step of mixing 4-(3-ethoxy-4-hydroxyphenyl)butan-2-one and xanthine compound (I) defined above, heated to a temperature of between 70 and 80° C., then a step of cooling to a temperature of between 15 and 28° C., then a step of addition of the mixture obtained previously with one or more additional ingredients, especially cosmetic or dermatological ingredients, such as those described above.

The invention is illustrated in greater detail in the example that follows. The amounts of the ingredients are expressed as weight percentages.

EXAMPLE 1: VISUAL APPEARANCE OF SEVERAL MIXTURES 11 mixtures of 4-(3-ethoxy-4-hydroxyphenyl)butan-2-one (ketone compound) and caffeine were produced in different proportions by weight described in the table below, by heating each of the mixtures to the temperature 75° C.±5° C. then allowing to cool to room temperature.

The appearance of the mixture at T0 was then observed by the naked eye, then the mixture was left stored at room temperature (23° C.) for 2 months and the appearance of the mixture was observed again at the end of storage. It was noted whether the mixture was liquid and homogeneous or else if it was not homogeneous, with the appearance of crystals.

The following results were obtained:

| Mixture | Ketone composition (% by weight) | Caffeine (% by weight) | Appearance at T0 | Appearance at T = 2 months at room T |
|---|---|---|---|---|
| M1 | 99.5 | 0.5 | liquid | liquid |
| M2 | 99 | 1 | liquid | liquid |
| M3 | 98 | 2 | liquid | liquid |
| M4 | 97 | 3 | liquid | liquid |
| M5 | 96 | 4 | liquid | liquid |
| M6 | 95 | 5 | liquid | liquid |
| M7 | 94 | 6 | liquid | crystals |
| M8 | 93 | 7 | crystals | crystals |
| M9 | 92 | 8 | crystals | crystals |
| M10 | 91 | 9 | crystals | crystals |
| M11 | 90 | 10 | crystals | crystals |

It was thus observed that the mixtures M1 to M6, containing 0.5 to 5% caffeine, are liquid and homogeneous at T0 and after 2 months of storage at room temperature, whereas the mixtures M7 to M11, containing 6 to 10% caffeine, are not homogeneous (appearance of crystals) after 2 months of storage at room temperature.

Thus, the mixtures M1 to M6 are appropriate for use in the industrial manufacture of compositions, especially of cosmetic compositions, by simple addition of the liquid mixture with the other constituents in order to obtain the final desired composition.

EXAMPLE 2

| | |
|---|---|
| Acrylates/$C_{10}$-$C_{30}$ alkyl acrylate crosslinked polymer (Carbopol ® Ultrez 20 Polymer from Noveon) | 0.9% |
| PEG-8 | 6% |
| Mixture M6 containing 95% by weight of 4-(3-ethoxy-4-hydroxyphenyl)butan-2-one and 5% by weight of caffeine | 0.53% |
| Sodium hydroxide | 0.35% |
| Water q.s. | |
| | 100% |

The composition is stable and homogeneous.

The invention claimed is:
1. A liquid mixture comprising 4-(3-ethoxy-4-hydroxyphenyl)butan-2-one and of xanthine compound (I):

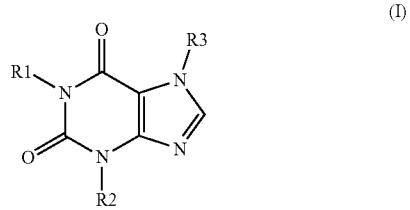

wherein:
R1, R2 and R3, independently of one another, denote a hydrogen atom or a methyl or ethyl radical; and
wherein the mixture comprises 4-(3-ethoxy-4-hydroxyphenyl)butan-2-one and the xanthine compound (I) in amounts such that the weight ratio of 4-(3-ethoxy-4-hydroxyphenyl)butan-2-one/xanthine compound (I) ranges from 17 to 250.

2. The mixture according to claim 1, wherein, for the compound (I), R1, R2 and R3, independently of one another, denote a hydrogen atom or a methyl radical.

3. The mixture according to claim 1, wherein the xanthine compound (I) is chosen from xanthine, caffeine, theobromine, theophylline and paraxanthine.

4. The mixture according to claim 1, wherein the xanthine compound (I) is caffeine.

5. The mixture according to claim 1, which comprises 4-(3-ethoxy-4-hydroxyphenyl)butan-2-one and the xanthine compound (I) in amounts such that the weight ratio of 4-(3-ethoxy-4-hydroxyphenyl)butan-2-one/compound (I) ranges from 17 to 200.

6. A process for preparing a liquid mixture comprising a step of mixing 4-(3-ethoxy-4-hydroxyphenyl)butan-2-one and a xanthine compound (I):

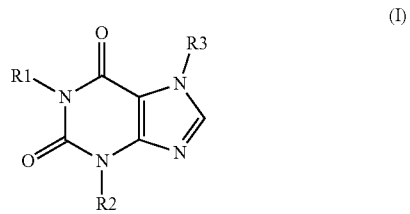

wherein:
R1, R2 and R3, independently of one another, denote a hydrogen atom or a methyl or ethyl radical;
heated to a temperature of between 70 and 80° C., and then a step of cooling to a temperature of between 15 and 28° C.; and
wherein the mixture comprises 4-(3-ethoxy-4-hydroxyphenyl)butan-2-one and the xanthine compound (I) in amounts such that the weight ratio of 4-(3-ethoxy-4-hydroxyphenyl)butan-2-one/xanthine compound (I) ranges from 17 to 250.

7. A composition comprising, in a physiologically acceptable medium, the liquid mixture of 4-(3-ethoxy-4-hydroxyphenyl)butan-2-one and of xanthine compound (I) according to claim 1.

8. The composition according to claim 7, which comprises at least one additional ingredient chosen from water, oils, polyols having from 1 to 10 carbon atoms, gelling agents, surfactants, film-forming polymers, colorants, fragrances, fillers, UV screening agents, plant extracts, cosmetic and dermatological active agents, and salts.

9. The composition according to claim 7, wherein the 4-(3-ethoxy-4-hydroxyphenyl)butan-2-one is present at an amount ranging from 0.01% to 5% by weight relative to the total weight of the composition.

10. A non-therapeutic cosmetic treatment process for caring for and/or making up and/or cleansing keratin materials, comprising the application to said keratin materials of a composition according to claim 7.

11. The mixture according to claim 2, wherein the xanthine compound (I) is chosen from xanthine, caffeine, theobromine, theophylline and paraxanthine.

12. The mixture according to claim 1, which comprises 4-(3-ethoxy-4-hydroxyphenyl)butan-2-one and the xanthine compound (I) in amounts such that the weight ratio of 4-(3-ethoxy-4-hydroxyphenyl)butan-2-one/compound (I) ranges from 17 to 100.

13. The mixture according to claim 2, which comprises 4-(3-ethoxy-4-hydroxyphenyl)butan-2-one and the xanthine compound (I) in amounts such that the weight ratio of 4-(3-ethoxy-4-hydroxyphenyl)butan-2-one/compound (I) ranges from 17 to 200.

14. The mixture according to claim 2, which comprises 4-(3-ethoxy-4-hydroxyphenyl)butan-2-one and the xanthine compound (I) in amounts such that the weight ratio of 4-(3-ethoxy-4-hydroxyphenyl)butan-2-one/compound (I) ranges from 17 to 100.

15. The mixture according to claim 3, which comprises 4-(3-ethoxy-4-hydroxyphenyl)butan-2-one and the xanthine compound (I) in amounts such that the weight ratio of 4-(3-ethoxy-4-hydroxyphenyl)butan-2-one/compound (I) ranges from 17 to 200.

16. The mixture according to claim 3, which comprises 4-(3-ethoxy-4-hydroxyphenyl)butan-2-one and the xanthine compound (I) in amounts such that the weight ratio of 4-(3-ethoxy-4-hydroxyphenyl)butan-2-one/compound (I) ranges from 17 to 100.

17. The mixture according to claim 4, which comprises 4-(3-ethoxy-4-hydroxyphenyl)butan-2-one and the xanthine compound (I) in amounts such that the weight ratio of 4-(3-ethoxy-4-hydroxyphenyl)butan-2-one/compound (I) ranges from 17 to 200.

18. The mixture according to claim 4, which comprises 4-(3-ethoxy-4-hydroxyphenyl)butan-2-one and the xanthine compound (I) in amounts such that the weight ratio of 4-(3-ethoxy-4-hydroxyphenyl)butan-2-one/compound (I) ranges from 17 to 100.

19. The composition according to claim 7, wherein the 4-(3-ethoxy-4-hydroxyphenyl)butan-2-one is present at an amount ranging from 0.01% to 3% by weight relative to the total weight of the composition.

20. The composition according to claim 7, wherein the 4-(3-ethoxy-4-hydroxyphenyl)butan-2-one is present at an amount ranging from 0.01% to 2.5% by weight relative to the total weight of the composition.

21. The mixture according to claim 1, wherein the xanthine compound (I) is present at an amount ranging from 0.5% to 5% by weight relative to the total weight of 4-(3-ethoxy-4-hydroxyphenyl)butan-2-one and of xanthine compound (I).

22. The process according to claim 6, wherein the xanthine compound (I) is present at an amount ranging from 0.5% to 5% by weight relative to the total weight of 4-(3-ethoxy-4-hydroxyphenyl)butan-2-one and of xanthine compound (I).

23. The composition according to claim 7, wherein the xanthine compound (I) is present at an amount ranging from 0.5% to 5% by weight relative to the total weight of 4-(3-ethoxy-4-hydroxyphenyl)butan-2-one and of xanthine compound (I).

\* \* \* \* \*